United States Patent [19]
Harral et al.

[11] Patent Number: 5,151,166
[45] Date of Patent: Sep. 29, 1992

[54] OXYGEN MONITORING METHOD AND APPARATUS

[75] Inventors: Michael W. Harral; Eric L. Rendell, both of Yeovil, England

[73] Assignee: Normalair-Garrett (Holdings) Limited, England

[21] Appl. No.: 591,231

[22] Filed: Oct. 1, 1990

[30] Foreign Application Priority Data

Oct. 2, 1989 [GB] United Kingdom ............... 8922126

[51] Int. Cl.⁵ ......................................... G01N 27/26
[52] U.S. Cl. .................................. 204/425; 204/426; 204/153.16
[58] Field of Search .................... 204/425, 426, 153.16

[56] References Cited

U.S. PATENT DOCUMENTS 4,231,733 11/1980 Hickam et al. ..................... 204/426

Primary Examiner—John Niebling
Assistant Examiner—Bruce F. Bell
Attorney, Agent, or Firm—Larson & Taylor

[57] ABSTRACT

The oxygen content of oxygen-enriched air is monitored by a solid electrolyte amperometric sensor which does not require a reference gas for comparison with the oxygen-enriched air. When oxygen-enriched air is supplied to the sensor a current signal is output by the sensor. The current signal is converted to a voltage signal which is processed by a signal processor storing an oxygen diffusion equation in the form of a look-up table to obtain an oxygen percentage concentration signal. An oxygen partial pressure signal may be obtained by supplying ambient pressure signals from an ambient pressure sensor to the signal processor for multiplication with the oxygen concentration signal.

14 Claims, 2 Drawing Sheets

OXYGEN MONITORING METHOD AND APPARATUS

BACKGROUND OF THE INVENTION

1. Field of the Invention

This invention relates to oxygen monitoring and is more particularly, but not exclusively, concerned with a method and apparatus for monitoring oxygen in oxygen-enriched air delivered by an aircraft on-board oxygen generating system.

2. Description of the Prior Art

The development and introduction of aircraft on-board oxygen generating systems (OBOGS) for supplying oxygen-enriched air for aircrew breathing has led to a requirement for airborne oxygen monitoring apparatus.

In an aircraft breathing system having an OBOGS which delivers air enriched with oxygen to maximum concentration (90-95%), the oxygen enriched air is diluted with ambient air at a breathing regulator before passing to a breathing mask, and the requirement is generally to monitor oxygen concentration. However, in an aircraft breathing system having an OBOGS which delivers air enriched with oxygen to a concentration appropriate to maintaining an oxygen partial pressure within a physiologically acceptable range of values throughout the altitude range of the aircraft without downstream dilution by ambient air, the requirement is generally to monitor oxygen partial pressure.

The first monitors used to meet these requirements were electro-chemical sensors operating on either galvanic (voltage output) or polarographic (current limiting) principles. These were versions of sensors produced for medical or analytical applications and suffered from a number of problems when operated in an aerospace environment. In particular, because consumable electrodes are used, output drifts with time giving rise to a requirement for frequent recalibration and overall life is limited. Also, the internal chemical processes of these sensors are strongly temperature dependent making it difficult to meet military specification requirements without complex temperature compensation and the use of external heaters.

Recognizing the limitations of electro-chemical sensors, the assignee of the present application (Normalair-Garrett) developed a flueric sensor which generates a switched output by comparing the physical properties of a sample gas (oxygen-enriched air in an aircraft breathing system) with those of a known reference gas (typically engine bleed air in an aircraft breathing system). Such sensors are disclosed in EP-A-0036285 and GB-A-2199166. Their wide operating temperature range (−40° to +70° C.), fast response (1 s) and long life (no moving parts) represent a considerable operational and logistic advantage compared with electro-chemical sensors.

More recently Normalair-Garrett have proposed (in U.S. Patent application Ser. No. 498,393 filed Mar. 26, 1990 but not published at the filing date of the present application) to use a zirconia cell oxygen concentration sensor for improved control of the concentration of oxygen in oxygen-enriched air delivered by an OBOGS throughout the operating altitude range of an aircraft. This sensor relies on the electrical properties of zirconia doped with yttria, at temperatures in excess of about 600° C. If a wafer of such doped zirconia is exposed to differing oxygen concentrations on its opposite sides, a small potential difference will be generated across it. Thus this sensor requires a supply of reference air for comparison with the oxygen-enriched air that is being monitored.

However, the requirement for reference air is a disadvantage because such sensors cannot be readily retrofitted in existing aircraft breathing systems which utilize electro-chemical sensors.

Also, in an operational situation where aircraft are queuing for take-off, the engine of one aircraft may be ingesting the exhaust of another aircraft so that a bleed of engine compressor air may not provide a stable reference.

The performance requirements for the next generation of aircraft are considerably more demanding which gives rise to a requirement for higher levels of performance from the oxygen monitor in terms of response rate, accuracy and stability.

Zirconia sensors operating on a current limiting (amperometric) principle requiring only a sample of the oxygen-enriched air to be monitored (see for example U.S. Pat. No. 4,839,019) have now become available. Such amperometric sensors output a limiting current having a logarithmic relationship to oxygen concentration. In applications, that require generally low concentrations of oxygen to be sensed, the non-linear logarithmic output is acceptable; however, in applications where high concentrations of oxygen, for example 90% or more, have to be monitored, such as is the case in aircraft aircrew oxygen-enriched breathing air supplied by an OBOGS, inaccuracies introduced by a sensor having a logarithmic output are unacceptable. At the same time, in addition to their advantage of operating without a reference gas, clear advantages are offered by amperometric sensors in the areas of overall size and power consumption which further assist in meeting space envelope requirements, when compared with sensors of the air reference type.

SUMMARY OF THE INVENTION

The present invention has for its object the provision of a method and apparatus for monitoring oxygen in oxygen-enriched air which will meet, substantially, the higher levels of performance required from oxygen monitors in the next generation of aircraft without a reference gas and which may be suited, therefore, for retrofit in existing aircraft breathing systems which presently embody electro-chemical sensors.

In one aspect the present invention provides a method of monitoring oxygen in oxygen-enriched air comprising the steps of:

supplying a sample of the oxygen-enriched air to solid electrolyte amperometric sensor means whereby a non-linear current signal having a logarithmic relationship with oxygen concentration is output by said sensor means;

converting the current signal output by the amperometric sensor means to a voltage signal;

processing the voltage signal in signal processing means storing an oxygen diffusion equation in the form of a look-up table;

and outputting a linear oxygen percentage concentration signal.

When a partial pressure of oxygen signal is required the method of the present invention is further characterised by the additional steps of multiplying the oxygen percentage concentration signal with an ambient pressure signal derived from pressure sensor means.

Means for processing the oxygen concentration and ambient pressure signals may output a digital signal and the method may comprise the further step of converting the digital signal to an analog signal which is directly proportional to oxygen partial pressure.

The method of the present invention may include the steps of activating a warning signal when the oxygen partial pressure falls below a predetermined value (e.g. 182 mmHg), and of inhibiting the warning above a predetermined aircraft cabin altitude (e.g. 9000 m) if the oxygen percentage is above a predetermined value (e.g. 85%).

In another aspect the present invention provides apparatus for monitoring oxygen in oxygen-enriched air comprising solid electrolyte amperometric sensor means, means for supplying a sample of the oxygen enriched air to said sensor means whereby a current signal is output by said sensor means, and means for converting the current signal to a voltage signal which is delivered to signal processing means storing an oxygen diffusion equation in the form of a look-up table, said signal processing means being adapted to process the voltage signal and output an oxygen percentage concentration signal.

In an embodiment of the invention the apparatus further comprises an ambient pressure sensor connected for supplying a pressure signal to the signal processing means which is further adapted to multiply the oxygen percentage concentration signal with the pressure signal and to output an oxygen partial pressure signal.

For the very high degree of accuracy required of apparatus suited for use in the next generation of aircraft the signal processing means will comprise a microprocessor; however, in applications where a lower degree of accuracy can be tolerated and, in particular, when an oxygen percentage concentration signal is required, the signal processing means may comprise analog circuitry.

The signal processing means may output the oxygen partial pressure signal in digital form and the apparatus may further comprise digital to analog converter means for generating a signal which is directly proportional to oxygen partial pressure.

The signal processing means of the apparatus in the aforementioned embodiment of the invention may be further adapted to activate a warning signal when the oxygen partial pressure falls below a predetermined value and to inhibit the warning above a predetermined cabin altitude if the oxygen percentage is above a predetermined value.

Apparatus for generating an oxygen partial pressure signal in accordance with a particular embodiment of the invention further comprises first and second multiplex and amplifier means connected with analog to digital converter means for selecting signals from the amperometric and pressure sensor means and feeding analog voltage signals to the signal processing means.

Some present day amperometric sensors may exhibit an error at the lower end of the temperature range required for aircraft operation, i.e. below −10° C.; however, we propose that this error may be corrected by inputting to the first multiplex means an ambient temperature signal from ambient temperature sensing means and providing a correction factor in the signal processing means.

Potential divider means adjustable by resistor means may be connected between the first and second multiplex and amplifier means for setting a full scale reading.

Means may be provided for adding small positive offset to the output of the second amplifier means so that negative offsets can be measured.

The processing means may be connected to circuit means for controlling heater means of the amperometric sensor means. The heater means may be connected as one arm of a four arm resistance bridge. The voltage of the heater means may be controlled by the processing means during warm-up in order to minimize sensor stress. The processing means may also receive a signal to indicate if the sensor is being maintained at its correct working temperature.

Because they operate on a gas diffusion principle it is possible that some amperometric sensors may exhibit a small but unacceptable instability in operating over the wide altitude range, typically 0 to 18000 meters (0 to 60000 feet), of the next generation of aircraft. In avoidance of any such potential problem we propose that the amperometric sensor of apparatus in accordance with the present invention may be located in a pressure chamber having means for maintaining the pressure of sample oxygen-enriched air in the chamber at a constant positive pressure differential of, for example, 34 kPa (5 PSIG) above aircraft cabin pressure, thereby ensuring that at maximum operational altitude adequate pressure is maintained for correct sensor operation.

Flow of oxygen-enriched air to the pressure chamber may be controlled by a solenoid operated valve which in normal operation of the apparatus is open to allow oxygen-enriched air to enter the chamber.

Pressure in the pressure chamber may be set by a pressure relief valve which opens to vent the chamber to ambient when the pressure exceeds the desired differential over cabin ambient pressure.

The solenoid valve and pressure relief valve may provide part of a press-to-test function for the apparatus. The solenoid valve is switched either directly or remotely so as to cut off the supply of sample oxygen-enriched air to the pressure chamber and communicate it instead with a primary nozzle of a jet pump. At the same time the sample oxygen-enriched air applies pressure to a diaphragm of the pressure relief valve causing the valve to open and communicating the pressure chamber with ambient by way of the jet pump. The jet pump is driven by the sample oxygen-enriched air and being in communication with the pressure chamber applies a suction to the chamber which causes an inward pressure relief valve to open and cabin air to be drawn into the chamber. This creates an oxygen partial pressure of 160 mm Hg or less and activates a warning indication thereby checking that the amperometric sensor is functioning.

Alternatively, pressure in the pressure chamber may be controlled by an aneroid valve having a valve face which modulates with a valve seat to maintain the required constant pressure differential over ambient pressure sensed by the aneroid.

The solid electrolyte amperometric sensor is preferably of the type in which a zirconia wafer doped with yttria carries porous electrodes on its opposite surfaces and a restrictor on one side limits the availability of oxygen-enriched air to the cathode electrode.

BRIEF DESCRIPTION OF THE DRAWINGS

The invention will now be further described by way of example and with reference to the accompanying drawings in which.

DETAILED DESCRIPTION OF THE DRAWINGS

Embodiments of a method and an apparatus in accordance with the present invention are suited for monitoring either the percentage concentration or the partial pressure of oxygen in oxygen-enriched air. Central to the invention is a solid electrolyte amperometric oxygen sensor which does not require a supply of reference gas for comparison with the oxygen-enriched air.

Figure 1:
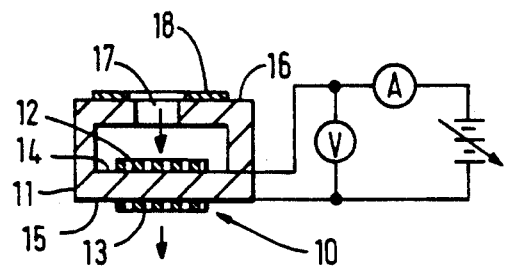
FIG. 1 is a diagrammatic representation of a solid zirconia electrolyte amperometric sensor suitable for use in apparatus in accordance with the invention.

One such oxygen sensor 10, reference FIG. 1, comprises an electrolyte provided by a wafer 11 of zirconia doped with yttria. The zirconia wafer 11 has porous electrodes 12, 13 attached to its opposite faces 14, 15, respectively, the electrode 12 being a cathode. A restrictor cap 16 having a diffusion hole 17 is provided on the cathode electrode 12 side of the wafer to limit the availability of oxygen-enriched air at the cathode. A heater 18 encompasses the diffusion hole 17 on the external surface of the cap 16 for maintaining a constant operating temperature. When a voltage V is applied across the wafer, the current flow is limited by the availability of oxygen ions. If the diffusion hole is sufficiently small, any oxygen entering the space above the cathode electrode is instantly pumped through the wafer and the oxygen concentration in this region is close to zero. Hence the limiting current depends only upon the flow behaviour of the diffusion hole and the surrounding oxygen concentration.

The limiting current (IL) is given by the equation:

$$IL = \frac{4F}{RT} \cdot \frac{D(O_2) \times S \times P}{l} \log e \left(1 - \frac{PPO_2}{P}\right)$$

Where:
F = Faraday Constant
R = Universal gas constant
T = Operating temperature
$D(O_2)$ = Oxygen diffusion coefficient of the gas mixture
S = Area of the diffusion hole
l = Length of the diffusion hole
P = Total pressure of gas mixture
$PPO_2$ = Partial pressure of oxygen In practice, the diffusion coefficient $D(O_2)$ is a function of ambient pressure and temperature such that over a limited range of conditions these terms cancel to give:

$$IL = K \log e (I - XO_2)$$

Where:
K = a constant
X = the volume percentage of oxygen

A solid electrolyte amperometric oxygen sensor of zirconia type offers the advantages of lower operating temperature, lower power consumption, and no requirement for reference gas, compared with potentiometric oxygen sensors.

Apparatus for monitoring oxygen partial pressure in accordance with one embodiment of the invention, reference FIG. 2, includes an oxygen sensor 20 of solid electrolyte amperometric type as hereinbefore described with reference to FIG. 1. A sample of oxygen-enriched air is supplied to the sensor 10 by means not shown in FIG. 2 and the sensor outputs a current signal having a logarithmic relationship to oxygen concentration. This current is passed through a resistor 21 to produce a voltage which is fed to a multiplexer 22 of first multiplex and amplifier means. The voltage dropped across the resistor 21 is small compared with the sensor driving voltage so that it does not affect its performance.

The multiplexer 22 also receives an ambient cabin pressure signal from a pressure sensor 23 and an ambient temperature signal from a temperature sensor 24. One pair of lines 25 into the multiplexer 22 are connected to zero volts, the reading from this input being subtracted from other measurements by processing means as will hereinafter be described.

Signals selected by the multiplexer 22 are amplified by an amplifier 26 of the first multiplex and amplifier means and fed to second multiplex and amplifier means comprising a multiplexer 27 and amplifier 28. A potential divider circuit 29 is connected between the first and second multiplex and amplifier means and includes an adjustable pressure sensor gain resistor 30 and an adjustable oxygen sensor gain resistor 31 for trimming the sensors 23 and 22, respectively, to set full scale reading. The multiplexer 27 also takes the output from a pressure sensor and oxygen sensor offset circuit 32 which is used to adjust for zero offset of the pressure sensor 23 and oxygen sensor 20.

Voltage signals from the multiplexer 27 are amplified by the amplifier 28 and a small positive voltage offset 33 is added to the output of amplifier 28 so that negative offsets can be measured. The output is then fed to an analog to digital converter 34 which changes the voltage signal to a digital form suitable for use by processing means which in this embodiment comprises a microprocessor 35.

The oxygen sensor heater 36 is connected as one arm of a four arm resistance bridge 37, the temperature of the heater being kept constant by controlling the voltage applied to the bridge to produce a balance by means of a heater control feedback circuit 38. The microprocessor controls the heater warm-up time to minimise heater stress by switching in different values of reference resistor.

The microprocessor 35 has two test inputs 39, 40 which are used to cause the signal from the pressure sensor 23 and oxygen sensor 20 to be output directly so that the two sensors can be calibrated independently by means of the potential divider circuit 29 and the offset circuit 32.

Operation of the apparatus is controlled by internal firmware stored in EPROM and executing in the microprocessor 35.

In operation the oxygen sensor 20 produces a limiting current having a logarithmic relationship to oxygen concentration. The firmware acquires this current as a voltage generated across the resistor 21 and converts it to a linear oxygen percentage concentration signal using the oxygen diffusion equation in the form of a look-up table. The resultant concentration is multiplied by the measured cabin pressure to obtain oxygen partial pressure.

The microprocessor 35 uses a digital to analog converter 41 to generate a signal output 42 which is directly proportional to oxygen partial pressure. The microprocessor is also adapted to activate a warning signal 43 whenever oxygen partial pressure falls below 182 mm Hg but at altitudes above 9000 meters (30000 feet) the warning signal is inhibited if the oxygen percentage is greater than 85%. The warning signal is forced permanently on if a failure is detected in the apparatus by a built-in-test (BIT) facility which continually monitors the status of various signals generated internally of the apparatus. If required the microprocessor may output these status signals at an output 44.

Figure 3:
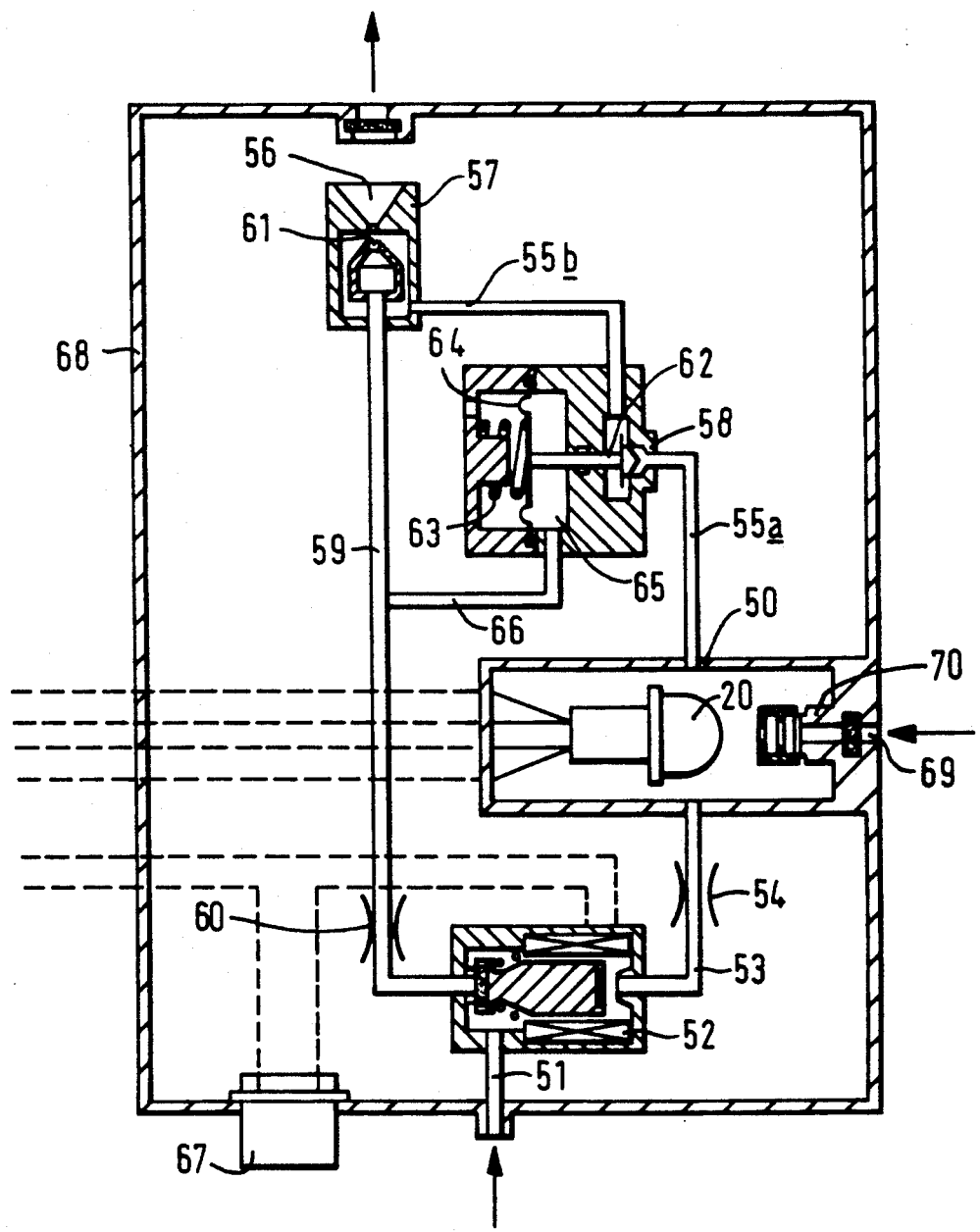
FIG. 3 is a schematic representation of a modification of the apparatus shown in FIG. 2 including a built-in-test facility.

A modified form of apparatus in accordance with the invention, as shown in FIG. 3, has the oxygen sensor 20 located in a sensor chamber 50 which during normal operation of the apparatus is maintained at a constant pressure differential of, say, 34 kPa above aircraft cabin pressure. This protects the sensor 20 against any instability in its operation which might otherwise occur over the wide operating altitude range, typically 0 to 18000 meters, required of the next generation of aircraft.

A sample of oxygen-enriched air delivered by an OBOGS (not shown) is supplied to the chamber 50 by way of a primary supply line 51, a solenoid valve 52 and a chamber supply line 53 which includes a flow restrictor orifice 54. Oxygen-enriched air is vented from the chamber 50 to ambient by way of vent lines 55a, 55b, of which vent line 55b connects the chamber with a secondary nozzle 56 of a jet pump 57. A pressure relief valve 58 is connected between the vent lines 55a and 55b. A jet pump supply line 59, including a flow restrictor orifice 60, connects between the solenoid valve 52 and a primary nozzle 61 of the jet pump 57.

The pressure relief valve 58 includes a valve member 62 which is urged by a spring 63 toward closing communication between the vent lines 55a and 55b whereby the pressure differential of 34 kPa over cabin pressure is maintained in the chamber 50 when the solenoid valve 52 is switched to allow sample oxygen-enriched air to flow to the chamber. The valve member 62 is carried by a diaphragm 64 which forms one wall of a chamber 65 provided internally of the pressure relief valve 58. The chamber 65 is connected by a branch line 66 with the jet pump supply line 59.

The solenoid valve 52 is switched to connect the primary supply line 51 with either the chamber supply line 53 or the jet pump supply lines 59 by a press-to-test switch 67 mounted on a housing unit 68 or by a remote switch (not shown).

The chamber 50 is provided as an integral part of the housing unit 68 and aircraft cabin air may enter the chamber 50 by way of an inlet 69 which is normally closed by an inwardly opening relief valve 70.

In normal operation of the apparatus the solenoid valve 52 is de-energised and connects the primary supply line 51 with the chamber supply line 53 whereby pressure is built up in the chamber 50. Pressure in the chamber holds the inwardly opening relief valve 70 in a position closing the inlet 69 and the valve member 62 of the pressure relief valve 58 is biased by the spring 63 to a position closing communication between the vent lines 55a and b. When pressure has been built up in the chamber 50 the valve member 62 of the pressure relief valve modulates to maintain the required pressure differential over cabin pressure.

Before commencement of operation of the apparatus a press-to-test function is activated by switching the press-to-test switch 67 to energise the solenoid valve 52 so that it connects the primary supply line 51 with the jet pump supply line 59 and closes communication between the primary supply line 51 and the chamber 50. Sample oxygen-enriched air is supplied by way of branch line 66 to the chamber 65 of the pressure relief valve 58 and pressure builds up therein to offload the spring 63 so that the valve member moves towards opening communication between the vent lines 55a and b whereby the sensor chamber 50 is communicated with the secondary nozzle 56 of the jet pump 57. The jet pump 57 driven by the sample oxygen-enriched air supplied to the primary nozzle 61 by way of supply line 59 evacuates the sensor chamber 50. When pressure in the sensor chamber 50 falls below cabin pressure the inwardly opening relief valve 58 is urged by cabin pressure to a position in which the sensor chamber is communicated with cabin pressure and cabin air is drawn into the sensor chamber. This creates an oxygen partial pressure of 160 mm Hg or less in the sensor chamber so that a warning indicator (not shown) is activated thereby demonstrating that the oxygen sensor 20 is functioning.

Figure 2:
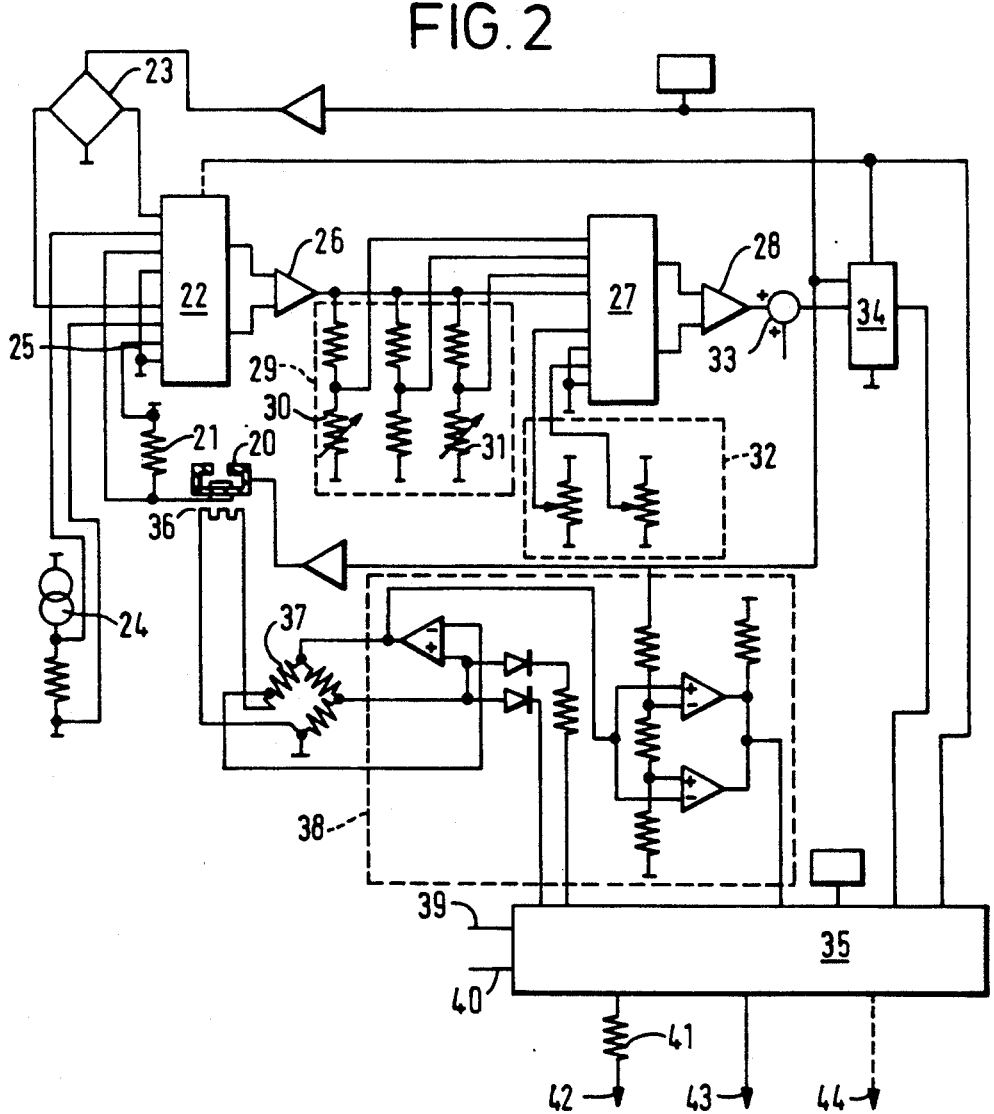
FIG. 2 is a circuit diagram of apparatus for monitoring oxygen partial pressure in accordance with one embodiment of the invention.

Apparatus suitable for monitoring oxygen concentration in accordance with a non-illustrated embodiment of the invention comprises a solid electrolyte amperometric sensor such as the oxygen sensor 20 of the apparatus shown in FIG. 2. However, the pressure sensor 23 is not required because there is no requirement for a pressure signal. Consequently the pressure sensor gain resistor 30 of the potential divider circuit 29 in FIG. 2 is not required and the offset circuit 32 need only provide for adjustment of the oxygen sensor. Also, if the oxygen sensor is one which exhibits satisfactory performance at the low end of the temperature range required of the apparatus then the ambient temperature sensor 24 of the apparatus shown in FIG. 1 is not required and the voltage signals derived from the oxygen sensor are fed direct to the first amplifier 26 with the first multiplexer 22 being omitted.

Whilst the processing means of such oxygen concentration monitoring apparatus may comprise a microprocessor, such as the microprocessor 35 of the FIG. 2 apparatus, signal processing could be carried out by suitable analog circuitry.

The method and apparatus for monitoring oxygen concentration or oxygen partial pressure as hereinbefore described with reference to and as shown in the accompanying drawings is not limited to utility in aircraft breathing systems. In particular, the method and apparatus for monitoring oxygen concentration in accordance with the present invention may be used to monitor the concentration of oxygen in oxygen-enriched air delivered by a molecular sieve oxygen concentration system for medical purposes.

What is claimed is:

1. A method of monitoring oxygen in oxygen-enriched air delivered by an aircraft on-board oxygen generating system comprising the steps of:

supplying a sample of oxygen-enriched air to solid amperometric sensor means whereby a non-linear current signal having a logarithmic relationship with oxygen concentration is output by said sensor means;

converting the current signal output by said sensor means to a voltage signal;

converting the voltage signal from analog to digital signal, processing the digital signal in signal processing means storing an oxygen diffusion equation in the form of a look-up table;

and outputting a linear oxygen percentage concentration signal for control and/or warning purposes.

2. A method according to claim 1, further comprising the steps of deriving an ambient pressure signal from pressure sensor means; and multiplying the oxygen concentration signal by the ambient pressure signal to obtain an oxygen partial pressure signal.

3. A method according to claim 2, further comprising the steps of outputting the oxygen partial pressure signal as a digital signal; and converting the digital signal to an analog signal which is directly proportional to oxygen partial pressure.

4. A method according to claim 3, further comprising the steps of activating a warning signal when the oxygen partial pressure falls below a predetermined value; and inhibiting the warning signal above a predetermined aircraft cabin altitude if the oxygen percentage concentration is above a predetermined value.

5. Apparatus for monitoring oxygen in oxygen-enriched air delivered by an aircraft on-board oxygen generating system comprising solid electrolyte amperometric sensor means, means for supplying a sample of oxygen-enriched air to said sensor means whereby a non-linear current signal having a logarithmic relationship with oxygen concentration is output by said sensor means, and means for converting the current signal to a voltage signal, means for converting the voltage signal from analog to digital signal, means for delivering the digital signal to signal processing means storing an oxygen diffusion equation in the form of a look-up table, said signal processing means being adapted to process the digital signal and output a linear oxygen percentage concentration signal for control and/or warning purposes.

6. Apparatus according to claim 5, further wherein said signal processing means is connected for receiving a pressure signal from ambient pressure sensor means and is further adapted to multiply the oxygen percentage concentration signal with the pressure signal and to output an oxygen partial pressure signal.

7. Apparatus according to claim 6, wherein first and second multiplex and amplifier means are connected with analog to digital converter means for selecting signals from the amperometric and pressure sensor means and for feeding analog voltage signals to said signal processing means.

8. Apparatus according to claim 7, wherein said first multiplex means is connected for receiving an ambient temperature signal from ambient temperature sensing means and a correction factor is provided in said signal processing means.

9. Apparatus according to claim 5, wherein said signal processing means is further connected to circuit means for controlling heater means of said sensor means.

10. Apparatus according to claim 5, wherein said apparatus is adapted for sensing oxygen content in oxygen-enriched air delivered to an aircraft aircrew member, and further comprises a pressure chamber housing said sensor means, and means for maintaining the pressure of sample oxygen-enriched air in said chamber at a constant positive pressure differential above aircraft cabin pressure.

11. Apparatus according to claim 10, wherein the flow of oxygen-enriched air into said pressure chamber is controlled by a solenoid operated valve which in normal operation of said apparatus is open to allow oxygen-enriched air to enter said pressure chamber.

12. Apparatus according to claim 11, wherein pressure in said pressure chamber is set by a pressure relief valve which opens to vent the chamber to ambient when the pressure exceeds the desired differential over cabin ambient pressure.

13. Apparatus as claimed in claim 12, wherein the solenoid operated valve and the pressure relief valve provide part of a press-to-test function for the apparatus.

14. Apparatus as claimed in claim 5, said amperometric sensor means is of the type having a zirconia wafer doped with yttria carrying porous electrodes on opposite surfaces thereof, and restrictor means on one side of said wafer for limiting the availability of oxygen-enriched air to a cathode one of said electrodes.

* * * * *